(12) United States Patent
Roddy

(10) Patent No.: US 11,519,263 B2
(45) Date of Patent: Dec. 6, 2022

(54) TRACEABLE MICRO-ELECTRO-MECHANICAL SYSTEMS FOR USE IN SUBTERRANEAN FORMATIONS

(71) Applicant: Halliburton Energy Services, Inc., Houston, TX (US)

(72) Inventor: Craig Wayne Roddy, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 25 days.

(21) Appl. No.: 15/536,522

(22) PCT Filed: Jan. 26, 2015

(86) PCT No.: PCT/US2015/012940
§ 371 (c)(1),
(2) Date: Jun. 15, 2017

(87) PCT Pub. No.: WO2016/122449
PCT Pub. Date: Aug. 4, 2016

(65) Prior Publication Data
US 2017/0356287 A1    Dec. 14, 2017

(51) Int. Cl.
*E21B 47/13* (2012.01)
*E21B 47/00* (2012.01)
(Continued)

(52) U.S. Cl.
CPC .............. *E21B 47/13* (2020.05); *E21B 43/16* (2013.01); *E21B 47/00* (2013.01); *E21B 47/005* (2020.05); *E21B 47/26* (2020.05); *G01N 29/2481* (2013.01); *G01N 33/383* (2013.01); *G01V 9/005* (2013.01); *G01V 15/00* (2013.01)

(58) Field of Classification Search
CPC ..... E21B 47/122; E21B 47/0005; E21B 47/00
See application file for complete search history.

(56) References Cited

U.S. PATENT DOCUMENTS 2,231,577 A    2/1941   Hare
5,572,021 A    11/1996  Heathman et al.
(Continued)

FOREIGN PATENT DOCUMENTS

WO    2012010821    1/2012
WO    2016007117    1/2016

OTHER PUBLICATIONS

Combine. (n.d.) American Heritage® Dictionary of the English Language, Fifth Edition. (2011). Retrieved May 1, 2020 from https://www.thefreedictionary.com/combine (Year: 2020).*
(Continued)

*Primary Examiner* — Blake Michener
*Assistant Examiner* — Theodore N Yao
(74) *Attorney, Agent, or Firm* — Thomas Rooney; C. Tumey Law Group PLLC

(57) ABSTRACT

Use of traceable micro-electro-mechanical systems ("MEMS") in subterranean formations. A method may comprise introducing a treatment fluid comprising a traceable micro-electro-mechanical system into a wellbore, wherein the traceable micro-electro-mechanical system comprises a micro-electro-mechanical system and a tagging material.

20 Claims, 3 Drawing Sheets

(51) Int. Cl.
*G01V 9/00* (2006.01)
*E21B 47/005* (2012.01)
*E21B 47/26* (2012.01)
*E21B 43/16* (2006.01)
*G01N 29/24* (2006.01)
*G01N 33/38* (2006.01)
*G01V 15/00* (2006.01)

(56) References Cited

U.S. PATENT DOCUMENTS

| | | | |
|---|---|---|---|
| 6,120,451 A | 9/2000 | Washburn et al. | |
| 6,162,176 A | 12/2000 | Washburn et al. | |
| 7,712,527 B2 | 5/2010 | Roddy | |
| 8,083,849 B2 | 12/2011 | Lewis et al. | |
| 8,100,177 B2 | 1/2012 | Smith et al. | |
| 8,162,050 B2 | 4/2012 | Roddy et al. | |
| 8,162,055 B2 | 4/2012 | Lewis et al. | |
| 8,291,975 B2 | 10/2012 | Roddy et al. | |
| 8,297,352 B2 | 10/2012 | Roddy et al. | |
| 8,297,353 B2 | 10/2012 | Roddy et al. | |
| 8,302,686 B2 | 11/2012 | Roddy et al. | |
| 8,316,936 B2 | 11/2012 | Roddy et al. | |
| 8,342,242 B2 | 1/2013 | Roddy et al. | |
| 8,555,967 B2 | 10/2013 | Chatterji et al. | |
| 9,580,637 B2 | 2/2017 | Gordon et al. | |
| 2004/0149431 A1 | 8/2004 | Wylie et al. | |
| 2006/0101916 A1 | 5/2006 | Griffiths et al. | |
| 2006/0131014 A1 | 6/2006 | Huang et al. | |
| 2007/0034373 A1* | 2/2007 | McDaniel | E21B 47/11 166/250.1 |
| 2008/0000687 A1* | 1/2008 | Xu | E21B 12/02 175/39 |
| 2010/0294496 A1 | 11/2010 | Woytowich et al. | |
| 2011/0187556 A1 | 8/2011 | Roddy et al. | |
| 2011/0192592 A1 | 8/2011 | Roddy et al. | |
| 2011/0192594 A1* | 8/2011 | Roddy | E21B 33/13 166/250.01 |
| 2011/0199228 A1 | 8/2011 | Roddy et al. | |
| 2013/0062068 A1 | 3/2013 | Roddy et al. | |
| 2013/0213647 A1 | 8/2013 | Roddy et al. | |
| 2013/0233538 A1* | 9/2013 | Chatterji | E21B 47/00 166/250.12 |
| 2013/0292109 A1* | 11/2013 | Smith, Jr. | E21B 43/04 166/250.1 |
| 2014/0083699 A1 | 3/2014 | Roddy et al. | |
| 2014/0111349 A1 | 4/2014 | Roberson et al. | |
| 2014/0219057 A1 | 8/2014 | Dallas et al. | |
| 2021/0047551 A1* | 2/2021 | Shirley | C09K 8/516 |
| 2021/0047902 A1* | 2/2021 | Yeh | E21B 43/10 |
| 2021/0047906 A1* | 2/2021 | Entchev | C09K 8/62 |

OTHER PUBLICATIONS

"Dope" definition available from: https://www.lexico.com/en/definition/dope (Year: 2020).*
"Integrate" definition available from: https://www.lexico.com/en/definition/integrate (Year: 2020).*
International Search Report and Written Opinion for PCT Application No. PCT/US2015/012940 dated Sep. 25, 2015.
"Neutron Logs Improve Interpretation of Foamed Cement, Even in Concentric Casing" Harness et al. published Dec. 1996.
International Search Report and Written Opinion for PCT/US2015/018095 dated Oct. 27, 2015.

* cited by examiner

TRACEABLE MICRO-ELECTRO-MECHANICAL SYSTEMS FOR USE IN SUBTERRANEAN FORMATIONS

BACKGROUND

This disclosure relates to subterranean operations, such as drilling, completing, servicing, and treating a subterranean well. In particular, the present disclosure relates to use of traceable micro-electro-mechanical systems ("MEMS") in operations in subterranean formations.

Natural resources such as gas, oil, and water residing in a subterranean formation or zone may be recovered by drilling a wellbore into the subterranean formation while circulating a drilling fluid in the wellbore. After terminating the circulation of the drilling fluid, a string of pipe (e.g., casing) may be run in the wellbore. The drilling fluid may then be circulated downward through the interior of the pipe and upward through the annulus, which is located between the exterior of the pipe and the walls of the wellbore (or larger conduit in the wellbore). Next, primary cementing may be performed whereby a cement composition may be placed in the annulus and permitted to set into a hard mass (i.e., sheath) that may support and position the pipe string in the wellbore and may bond the exterior surface of the pipe string to the wellbore walls (or to the larger conduit). Subsequent secondary cementing operations may also be performed. Example of such secondary cementing operations may include the placement of a cement plug or squeeze cementing for sealing voids in a pipe string, cement sheath, gravel pack, subterranean formation, and the like.

MEMS may be included in a cement composition placed into the wellbore. Among other things, the MEMS may include one or more sensors to provide information about the cement composition as well as wellbore conditions. In order to improve the quality of the sensed data, it may be desirable to determine the location of the MEMS in the cement composition. Current techniques for determining sensor position may include use of an interrogator tool that needs to be run into the wellbore. The interrogator tool may traverse all or a portion of the wellbore containing the MEMS. Data received by the interrogator tool may be used to determine the location of the MEMS. However, a separate trip into the wellbore by the interrogator tool may consume valuable time and expense in a well operation.

BRIEF DESCRIPTION OF THE DRAWINGS

These drawings illustrate certain aspects of some examples of the present invention, and should not be used to limit or define the invention.

DETAILED DESCRIPTION

Figure 1:
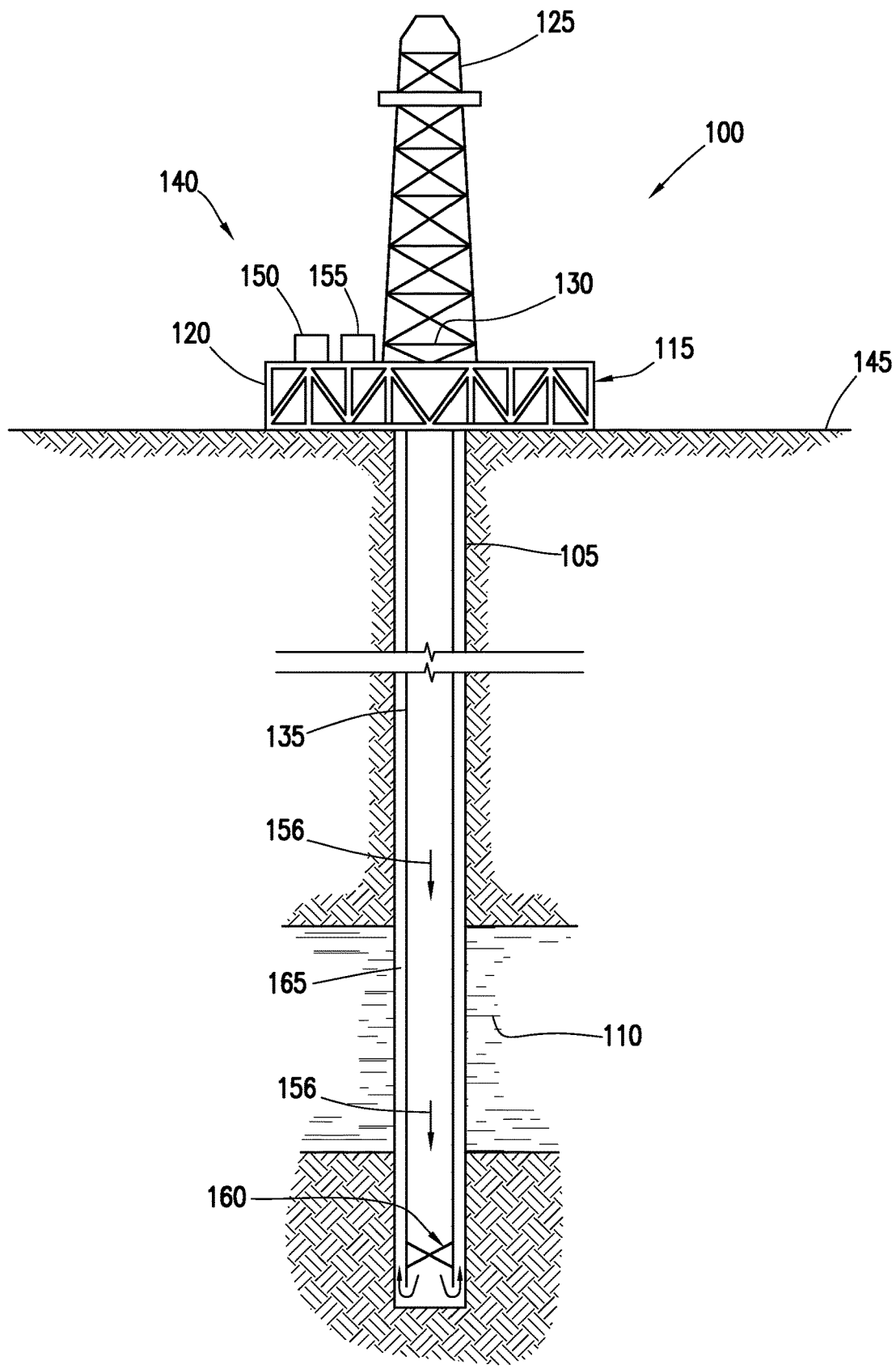
FIG. 1 is a schematic diagram illustrating an example system for delivery of treatment fluids into a wellbore.

Disclosed herein are traceable MEMS for use in subterranean operations, such as treatment fluids used in drilling, completing, servicing, and treating a subterranean well. A traceable MEMS may comprise a MEMS that has been combined with a tagging material, such as a thermal neutron absorbing material. Use of the tagging material in combination with the MEMS may provide a means for determining location of the traceable MEMS in a subterranean formation, as well as the location of the treatment fluid, for example, the location of the top of a cement composition. Advantageously, location of the traceable MEMS can be determined while logging and without the use of an interrogator tool. In addition, once the traceable MEMS are logged, their location may be used in conjunction with data later provided by the traceable MEMS with respect to wellbore conditions.

MEMS devices are well known, e.g., a semiconductor device with mechanical features on the micrometer scale. MEMS embody the integration of mechanical elements, sensors, actuators, and electronics on a common substrate. The substrate may comprise silicon. MEMS elements may include mechanical elements which are movable by an input energy (electrical energy or other type of energy). Using MEMS, a sensor may be designed to emit a detectable signal based on a number of physical phenomena, including thermal, biological, optical, chemical, and magnetic effects or stimulation. MEMS devices are minute in size, have low power requirements, are relatively inexpensive and are rugged, and thus may be well suited for use in subterranean operations. The MEMS may contain passive sensors that do not require continuous power from a battery or an external source in order to transmit real-time data.

The MEMS may comprise an active material connected to (e.g., mounted within or mounted on the surface of) an enclosure, the active material being able to respond to a wellbore parameter, and the active material being operably connected to (e.g., in physical contact with, surrounding, or coating) a capacitive MEMS element. Suitable active materials, such as dielectric materials, that respond in a predictable and stable manner to changes in parameters over a long period may be identified according to methods well known in the art. The MEMS may sense one or more parameters within the wellbore. Examples of the sensed parameters may include temperature, pH, moisture content, ion concentration (e.g., chloride, sodium, and/or potassium ions), or combinations thereof. The MEMS may also sense well cement characteristic data such as stress, strain, or combinations thereof. The MEMS may comprise active materials that respond to two or more measurands. In such a way, two or more parameters may be monitored.

The MEMS may be coupled with radio frequency identification devices (RFIDs) and may thus be able to detect and transmit parameters and/or well cement characteristic data for monitoring the cement during its service life. RFIDs may combine a microchip with an antenna (the RFID chip and the antenna are collectively referred to as the "transponder" or the "tag"). The antenna may provide the RFID chip with power when exposed to a narrow band, high frequency electromagnetic field from a transceiver. A dipole antenna or a coil, depending on the operating frequency, may be connected to the RFID chip and power the transponder when current is induced in the antenna by an RF signal from the transceiver's antenna. Such a device may be able to return a unique identification "ID" number by modulating and re-radiating the radio frequency (RF) wave. Passive RF tags are gaining widespread use due to their low cost, indefinite life, simplicity, efficiency, ability to identify parts at a distance without contact (tether-free information transmission ability). These robust and tiny tags may be attractive from an environmental standpoint as they require no battery.

The MEMS and RFID tag may be integrated into a single component (e.g., chip or substrate), or may alternatively be separate components operably coupled to each other. In an embodiment, an integrated, passive MEMS/RFID may contain a data sensing component, an optional memory, and an RFID antenna, whereby excitation energy is received and powers up the sensor, thereby sensing a present condition and/or accessing one or more stored sensed conditions from memory and transmitting same via the RFID antenna.

Within the United States, commonly used operating bands for RFID systems center on one of the three government assigned frequencies: 125 kHz, 13.56 MHz or 2.45 GHz. A fourth frequency, 27.125 MHz, has also been assigned. When the 2.45 GHz carrier frequency is used, the range of an RFID chip can be many meters. While this is useful for remote sensing, there may be multiple transponders within the RF field. In order to prevent these devices from interacting and garbling the data, anti-collision schemes may be used, as are known in the art. The MEMS may be integrated with local tracking hardware to transmit their position as they flow within a cement composition. The MEMS may form a network using wireless links to neighboring data sensors and have location and positioning capability through, for example, local positioning algorithms as are known in the art. The MEMS may organize themselves into a network by listening to one another to better enable communication.

The MEMS may be ultra-small, e.g., 3 mm$^2$ or smaller, such that they are pumpable in a treatment fluid, such as a cement composition. The MEMS may be approximately 0.01 mm$^2$ to 1 mm$^2$, alternatively 1 mm$^2$ to 3 mm$^2$, alternatively 3 mm$^2$ to 5 mm$^2$, or alternatively 5 mm$^2$ to 10 mm$^2$. Where MEMS may be used in cement compositions, the MEMS may be capable of providing data throughout the cement service life. The MEMS may be capable of providing data for up to 100 years. The treatment fluid may comprise an amount of MEMS effective to measure one or more desired parameters. The treatment fluid (e.g., cement composition) may comprises an effective amount of MEMS such that sensed readings may be obtained at intervals of about 1 foot, alternatively about 6 inches, or alternatively about 1 inch, along the portion of the wellbore containing the MEMS. Alternatively, the MEMS may be present in the treatment fluid in an amount of from about 0.01 to about 5 weight percent.

As previously described, traceable MEMS may comprise MEMS that has been combined with a tagging material. The tagging material may be embedded within the MEMS, incorporated into the housing thereof, or attached to the outer surface thereof. Suitable tagging materials may comprise relatively inert materials and/or also materials that are thermal neutron absorbing materials. The tagging materials may be inert to the chemical and physical properties of the MEMS and/or the treatment fluid. It may be desired that the tagging materials cause no significant changes in the conventional, desirable function of the MEMS and/or the properties of treatment fluid.

Thermal neutron absorbing materials may comprise any element which has a thermal neutron absorbing capability of a magnitude such that differences in the backscattered thermal neutrons before and after the traceable MEMS is introduced into a well bore can be detected. Example embodiments may comprise thermal neutron absorbing materials for use with neutron logging devices, however, tagging materials may comprise a variety of materials including those known in the art. Examples of suitable thermal neutron absorbing materials include cadmium, boron, gadolinium, iridium, and mixtures thereof. The boron may comprise boron carbide, boron nitride, boric acid, high boron concentrated glass, zinc borate, borax, and mixtures thereof. The gadolinium may comprise gadolinium oxide, gadolinium hydroxide, gadolinium acetate, high gadolinium concentrated glass, and mixtures thereof.

The traceable MEMS may be mixed with the treatment fluid by one of a variety of methods known to those of ordinary skill in the art. For example, the traceable MEMS may be mixed with a dry material (e.g., dry blended with cement), mixed with one or more liquid components (e.g., a carrier fluid such as water or a non-aqueous fluid), or combinations thereof. The mixing may occur onsite, for example, addition of the traceable MEMS into a bulk mixer, such as a cement slurry mixer. The traceable MEMS may be added directly to the bulk mixer, may be added to one or more component streams and subsequently fed to the bulk mixer, may be added downstream of the bulk mixer, or combinations thereof. In one specific example, the traceable MEMS may be added after a blending unit and slurry pump, for example, through a lateral by-pass. The traceable MEMS may be metered in and mixed onsite or may be pre-mixed into the treatment fluid (or one or more components thereof) and subsequently transported to the well site. For example, the traceable MEMS may be dry blended with cement and then transported to the well site where a cement composition may be formed comprising the traceable MEMS. Alternatively or additionally, the traceable MEMS may be pre-mixed with one or more liquid components (e.g., mix water) and transported to a well site where a cement composition may be formed comprising the traceable MEMS. The properties of the treatment fluid or components thereof may be such that the traceable MEMS distributed or dispersed therein do not substantially settle during transport or placement.

The treatment fluids may be any composition that may be prepared or otherwise provided at the surface and placed down the wellbore, typically by pumping. Without limitation, treatments fluids may include any fluid used to drill, complete, work over, fracture, repair, treat, or in any way prepare or service a wellbore for the recovery of materials residing in a subterranean formation penetrated by the wellbore. Examples of treatment fluids may include drilling fluids, fracturing fluids, completion fluids, spacer fluids, lost circulation fluids, displacement fluids, or drill-in fluids. The treatment fluid may comprise a carrier fluid, which may be an aqueous or non-aqueous carrier fluid, for example, and the traceable MEMS. The traceable MEMS may be suspended in, or otherwise disposed in, the carrier fluid.

Cement compositions in which the traceable MEMS may be included may comprise cement and water. Those of ordinary skill in the art will appreciate that the cement compositions generally should have a density suitable for a particular application. By way of example, the cement compositions may have a density of about 4 pounds per gallon ("lb/gal") to about 20 lb/gal. The cement compositions may be foamed or unfoamed or may comprise other means to reduce their densities, such as hollow microspheres, low-density elastic beads, or other density-reducing additives known in the art. Weighting agents may be used to increase the density of the cement composition. Those of ordinary skill in the art, with the benefit of this disclosure, will recognize the appropriate density for a particular application.

Any of a variety of cements suitable for use in subterranean cementing operations may be used. Suitable examples include hydraulic cements that comprise calcium, aluminum, silicon, oxygen and/or sulfur, which set and harden by reaction with water. Examples of such hydraulic cements, include, but are not limited to, Portland cements, pozzolana cements, gypsum cements, high-alumina-content cements, slag cements, silica cements, and combinations thereof. The hydraulic cement may comprise a Portland cement. The Portland cements may be classified as Classes A, C, H, or G cements according to American Petroleum Institute, *API Specification for Materials and Testing for Well Cements*, API Specification 10, Fifth Ed., Jul. 1, 1990. In addition, the hydraulic cement may include cements classified as ASTM Type I, II, or III.

The water may be from any source provided that it does not contain an excess of compounds that may undesirably affect other components in the cement composition. The water may comprise fresh water or salt water. Salt water generally may include one or more dissolved salts therein and may be saturated or unsaturated as desired for a particular application. Seawater or brines may be suitable for use in some applications. Further, the water may be present in an amount sufficient to form a pumpable fluid, for example, the water may be present in the treatment fluids in an amount in the range of from about 33% to about 200% by weight of the cement and, alternatively, from about 35% to about 70% by weight of the cement. With the benefit of this disclosure one of ordinary skill in the art should recognize the appropriate amount of water for a chosen application.

Other additives suitable for use in subterranean cementing operations also may be added to the cement compositions as deemed appropriate by one of ordinary skill in the art. Examples of such additives include, but are not limited to, strength-retrogression additives, set accelerators, set retarders, weighting agents, lightweight additives, gas-generating additives, mechanical property enhancing additives, lost-circulation materials, dispersants, fluid loss control additives, defoaming agents, foaming agents, thixotropic additives, and combinations thereof. Specific examples of these, and other, additives include silica (e.g., crystalline silica, amorphous silica, fumed silica, etc.), salts, fibers, hydratable clays, shale (e.g., calcined shale, vitrified shale, etc.), microspheres, diatomaceous earth, natural pozzolan, resins, latex, combinations thereof, and the like. Other optional additives may also be included, including, but not limited to, cement kiln dust, lime kiln dust, fly ash, slag cement, shale, zeolite, metakaolin, pumice, perlite, lime, silica, rice husk ash, small-particle size cement, combinations thereof, and the like. A person having ordinary skill in the art, with the benefit of this disclosure, should readily be able to determine the type and amount of additive useful for a particular application and desired result.

The treatment fluid comprising the traceable MEMS may be introduced into a wellbore. For example, the traceable MEMS may extend along all or a portion of a length of a wellbore annulus, such as a space between a casing or other conduit and a subterranean formation or a space between a casing (or other conduit) and a large conduit. The treatment fluid may be placed into the wellbore as part of a subterranean operation. Where cement compositions are used, the cement composition comprising the traceable MEMS may be placed into the wellbore as part of a primary cementing, secondary cementing, or other cementing operation.

The position of the traceable MEMS may be determined after placement in the wellbore. For example, a log may be run in the wellbore that can detect the location of the traceable MEMS. The log may be a neutron log. Running the neutron log may include emitting fast neutrons into the wellbore. Conventional dual-spacing neutron tools (commonly referred to as DSN tools) are well known in the art and have been utilized heretofore for running neutron logs of subterranean formations. Such DSN tools may include a neutron source for emitting fast neutrons, a long spacing thermal neutron detector and a short spacing thermal neutron detector. The DSN tool or another tool containing a source form which fast neutrons may be emitted may be lowered into the wellbore whereby the fast neutrons interact with elements in the wellbore and may be thermalized thereby. The thermal neutrons produced may be backscattered in the wellbore and may be detected by a thermal neutron detector on the DSN tool or another tool. The detector may generate a count representative of the detected thermal neutrons over one or more selected longitudinal subterranean intervals in the wellbore, e.g., the interval or intervals in the wellbore where it is expected that traceable MEMS will be located.

The subterranean locations of the traceable MEMS may be determined based on the differences in the count generated after their introduction and a count representative of the one or more subterranean intervals in the well before their introduction. That is, because the tagging material in the traceable MEMS absorbs some of the thermal neutrons as they are generated in the wellbore after their introduction, a comparison of the before and after counts correlated with the locations where the counts were generated should indicate the subterranean locations of the traceable MEMS. A thermal neutron count over the locations of interest in a wellbore before introduction of the traceable MEMS may be available as a result of the performance of previous treatments therein, etc. If not, a before introduction count may be determined prior to introducing the traceable MEMS into the wellbore. That is, a tool containing a fast neutron source may be lowered in the wellbore whereby the fast neutrons interact with elements in the wellbore and are thermalized. The thermal neutrons produced and backscattered in the wellbore may be detected by a thermal neutron detector as described above, and a count representative of the detected thermal neutrons over the one or more selected subterranean intervals in the wellbore may be produced.

In the wellbore, the traceable MEMS may be used for data gathering. The gathered data may be correlated with the determined position of the traceable MEMS in the wellbore. Data may be gathered continuously or intermittently after (and/or during) placement of the traceable MES in the wellbore. The data gathering may be carried out at the time of initial placement, for example, during drilling (e.g., drilling fluid comprising MEMS) or during cementing (e.g., cement composition comprising MEMS). Data gathering may also be carried out at one or more times subsequent to the initial placement of the traceable MEMS into the wellbore. For example, data gathering may be carried out at the time of initial placement in the wellbore or shortly thereafter to provide a baseline data set. As the wellbore is operated for recovery of natural resources over a period of time, data may be gathered at additional times. The data gathered over time may be compared to the baseline data and such comparison may indicate the overall condition of the wellbore. For example, changes in one or more sensed parameters may indicate one or more problems in the wellbore. Alternatively, consistency or uniformity in sensed parameters may indicate no substantive problems in the wellbore. Data (e.g., sealant parameters) from a plurality of monitoring intervals may be plotted over a period of time, and a resultant graph may be provided showing an operating or trend line for the sensed parameters. Atypical changes in the graph as indicated for example by a sharp change in slope or a step change on the graph may provide an indication of one or more present problems or the potential for a future problem. Accordingly, remedial and/or preventive treatments or services may be applied to the wellbore to address present or potential problems.

The traceable MEMs may be used, for example, to monitor the integrity and performance of a treatment fluid (e.g., a cement composition) over the life of the wellbore. Performance may be indicated by changes, for example, in various parameters, including, but not limited to, moisture content, temperature, pH, and various ion concentrations (e.g., sodium, chloride, and potassium ions) of the cement composition. The traceable MEMS may be included in the cement composition and parameters of the set cement composition in the wellbore may be monitored during placement and/or during life of the wellbore.

The traceable MEMS may be used, for example, in determining location of the top of a cement composition. As an example, in a primary cementing operation where a conduit, such as a casing or liner, is to be cemented in place in a well bore, a cement composition comprising traceable MEMS may be pumped downhole through the conduit and then upwardly into the annulus between the conduit and the walls of the well bore. Once the cement composition has been placed in the annulus, it may be important to verify that the cement composition has uniformly filled the annulus over the entire length of casing or liner being cemented. At least a portion of the cement composition may comprise the traceable MEMS. For example, the first portion of the cement composition introduced into the well bore may comprise the traceable MEMS so that the top of the cement column in the annulus should comprise the traceable MEMS. The tagging material may then allow the use of well bore logging devices to determine the location of the top of cement based on the presence of the traceable MEMS in the wellbore.

Turning now to FIG. 1, an example well system 100 for introduction of treatment fluids described herein into a wellbore 105 is shown. As illustrated, the wellbore 105 may be drilled into one or more subterranean formations 110. While the wellbore 105 is shown extending generally vertically into the one or more subterranean formations 110, the principles described herein are also applicable to wellbores that extend at an angle through the one or more subterranean formations 110, such as horizontal and slanted wellbores. As illustrated, a rig 115 may be disposed above the wellbore 105. The rig 115 may include a workdeck 120 that supports a derrick 125. Derrick 125 may support a hoisting apparatus 130 for raising and lower strings of pipe, such as casing 135.

As illustrated, the well system 100 may further include a fluid handling system 140 for introducing a treatment fluid into the wellbore 105 by way of a tubular, such as casing 135. In the illustrated embodiment, the fluid handling system 110 is above the surface 145 while wellbore 105 and casing 135 are below the surface 145. The fluid handling system 140 can be configured as shown in FIG. 1 or in a different manner, and may include additional or different features as appropriate. The fluid handling system 145 may be deployed via skid equipment, marine vessel deployed, or may be comprised of sub-sea deployed equipment.

Fluid handling system 110 may include mobile vehicles, immobile installations, skids, hoses, tubes, fluid tanks or reservoirs, pumps, valves, and/or other suitable structures and equipment. For example, the fluid handling system 110 may include pumping equipment 150 and a fluid supply 155, which both may be in fluid communication with the casing 135 or other tubular. The fluid supply 155 may contain the treatment fluid. The pumping equipment 150 may be used to supply treatment fluid from the fluid supply 155, which may include tank, reservoir, connections to external fluid supplies, and/or other suitable structures and equipment. While not illustrated, the fluid supply 155 may contain one or more components of the treatment fluid in separate tanks or other containers that may be mixed at any desired time. Pumping equipment 150 may be in fluid communication with the casing 135 to communicate treatment fluid into wellbore 105. Fluid handling system 140 may also include surface and down-hole sensors (not shown) to measure pressure, rate, temperature and/or other parameters of treatment. Fluid handling system 140 may include pump controls and/or other types of controls for starting, stopping and/or otherwise controlling pumping as well as controls for selecting and/or otherwise controlling fluids pumped during the injection treatment. An injection control system may communicate with such equipment to monitor and control the injection treatment.

With continued reference to FIG. 1, the well system 100 may be used for delivery of a treatment fluid comprising traceable MEMS (e.g., a cement composition comprising traceable MEMS) into the wellbore. As indicated by arrows 156, the treatment fluid comprising traceable MEMS may be pumped from fluid supply 155 down the interior of casing 135 in wellbore 105. The treatment fluid may be allowed to flow down the interior of the casing 135 through the casing shoe 160 at the bottom of the casing 135 and up around the casing 135 into the wellbore annulus 165. While not illustrated, other techniques may also be utilized for introduction of the treatment fluid. By way of example, reverse circulation techniques may be used that include introducing a treatment fluid comprising traceable MEMS (e.g., a cement composition comprising traceable MEMS) into the subterranean formation 110 by way of the wellbore annulus 165 instead of through the casing 135.

Figure 2:
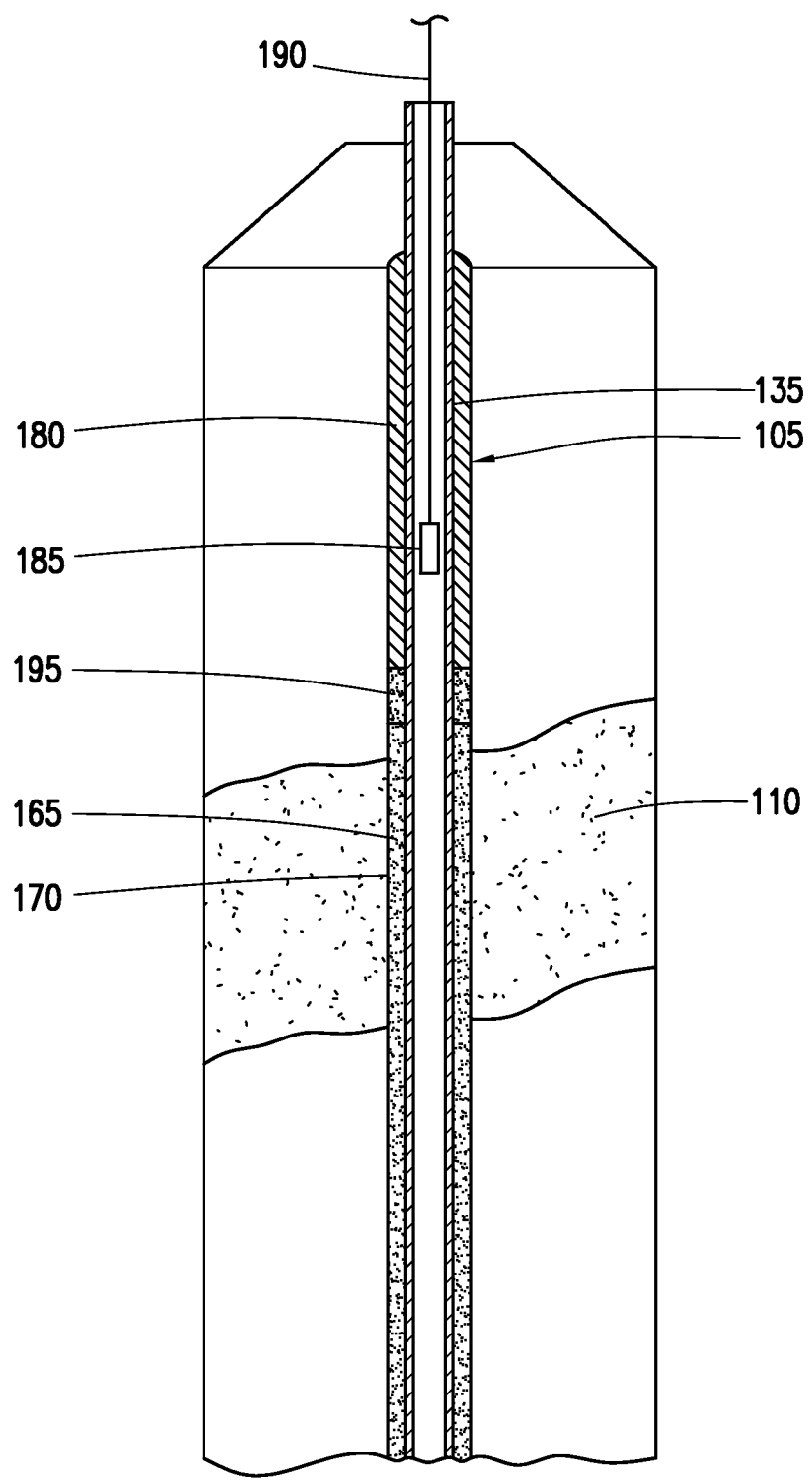
FIG. 2 is a schematic diagram illustrating example use of a logging tool for determining location of MEMS in a wellbore.

Turning now to FIG. 2, a treatment fluid 170, such as a cement composition, comprising a traceable MEMS may be pumped into the wellbore 105 so that the treatment fluid 170 may be positioned in the wellbore annulus 165 between the one or more subterranean formations 110 and the casing 135. The traceable MEMS may be disposed in all or a portion of the treatment fluid 170. As illustrated in FIG. 2, a spacer fluid 180 may be disposed in the wellbore annulus 165 above the treatment fluid 170. In an embodiment, the spacer fluid 180 may also contain traceable MEMS. As previously described, a logging tool 185, which may be a DSN tool, may be placed into the wellbore 105. As illustrated, the logging tool 185 may be placed within casing 135 of the wellbore 105. The logging tool 185 may be suspended within casing 135 by way of conveyance string 190. Conveyance string 190 may comprise, without limitation, a wireline cable, a slickline cable, coiled tubing, etc. Conveyance string 190 may provide support for logging tool 185 and may also couple logging tool 185 to a computer system (not shown). Alternatively, the computer system may be in wireless communication with logging tool 185. As previously described, the logging tool 185 may emit neutrons with corresponding measurements from which a log may be generated. From this log, the location of the traceable MES in the wellbore annulus 165 may be determined. For example, the top of cement 190 may be determined based on the location of the traceable MEMS in the wellbore annulus 165. The top of cement 195 may be determined by analyzing the location of the traceable MEMS in the wellbore annulus 165. Where MEMS are disposed in the treatment fluid 170 and not the spacer fluid 180, the top of the cement 195 may be indicated by the absence of the traceable MES in the wellbore annulus 165 in that absence of the traceable MEMS should indicate the end of the beginning of the spacer fluid 180 without the traceable MEMS.

Figure 3:
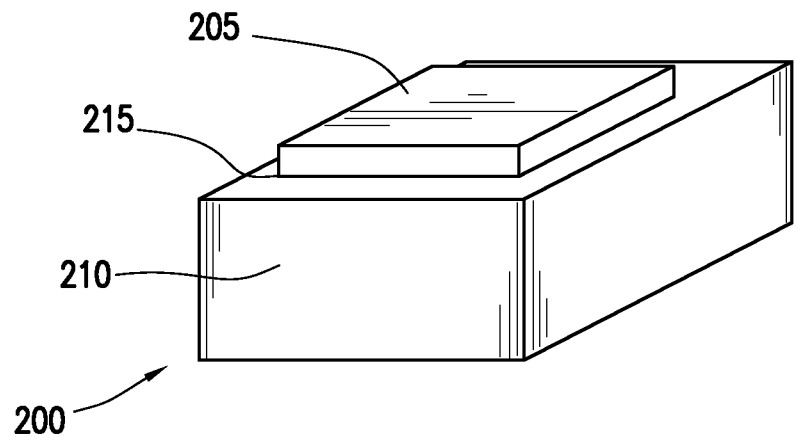
FIG. 3 is a schematic diagram illustrating an example traceable MEMS comprising a tagging material.
Figure 4:
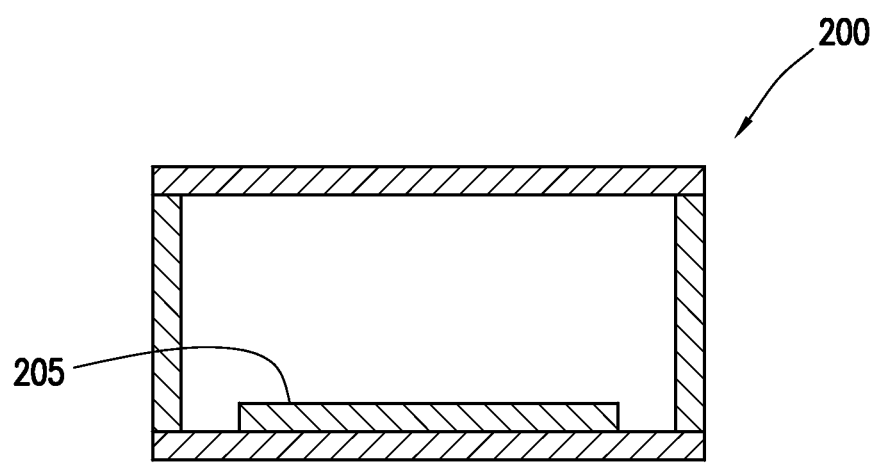
FIG. 4 is a schematic diagram illustrating another example traceable MEMS comprising a tagging material.

As previously described, the traceable MEMS may comprise MEMS that has been combined with a tagging material. The tagging material may be embedded within the MEMS, incorporated into the housing thereof, or attached to the outer surface thereof. Suitable tagging materials may comprise relatively inert materials and/or also materials that are thermal neutron absorbing materials. FIGS. 3 and 4 illustrate different configurations of traceable MES 200 that comprise a tagging material 205. As illustrated by FIG. 3, the traceable MEMS 200 may comprise a housing 210 having an outer surface 215. The tagging material 205 may be attached to the outer surface 215 of the housing 210. As illustrated by FIG. 4, the traceable MEMS 200 may be embedded inside the housing 210. Alternatively, the tagging material 205 may be incorporated into the housing 210 such that the tagging material 205 is integral with the housing 210. For example, the housing 210 may be formed partially or entirely from the tagging material 205.

The exemplary traceable MEMS disclosed herein may directly or indirectly affect one or more components or pieces of equipment associated with the preparation, delivery, recapture, recycling, reuse, and/or disposal of the disclosed traceable MEMS. For example, the traceable MEMS may directly or indirectly affect one or more mixers, related mixing equipment, mud pits, storage facilities or units, composition separators, heat exchangers, sensors, gauges, pumps, compressors, and the like used generate, store, monitor, regulate, and/or recondition the exemplary traceable MEMS and fluids containing the same. The disclosed traceable MEMS may also directly or indirectly affect any transport or delivery equipment used to convey the traceable MEMS to a well site or downhole such as, for example, any transport vessels, conduits, pipelines, trucks, tubulars, and/or pipes used to compositionally move the traceable MEMS from one location to another, any pumps, compressors, or motors (e.g., topside or downhole) used to drive the traceable MEMS, or fluids containing the same, into motion, any valves or related joints used to regulate the pressure or flow rate of traceable MEMS (or fluids containing the same), and any sensors (i.e., pressure and temperature), gauges, and/or combinations thereof, and the like. The disclosed traceable MEMS may also directly or indirectly affect the various downhole equipment and tools that may come into contact with the traceable MEMS such as, but not limited to, wellbore casing, wellbore liner, completion string, insert strings, drill string, coiled tubing, slickline, wireline, drill pipe, drill collars, mud motors, downhole motors and/or pumps, cement pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described and depicted above in FIGS. 1 and 2.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in Willis of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A method comprising:
   introducing a treatment fluid comprising a traceable micro-electro-mechanical system into a wellbore, wherein the traceable micro-electro-mechanical system comprises a micro-electro-mechanical system comprising a housing, wherein the housing comprises an outer surface with one or more sides, wherein the one or more sides consists of a first side and a plurality of remaining sides, wherein at least one thermal neutron absorbing material is incorporated into the housing thereof or attached to the outer surface of the housing thereof, wherein the first side comprises the at least one thermal neutron absorbing material, and wherein the plurality of remaining sides do not comprise the at least one thermal neutron absorbing material;

running a neutron log in the wellbore to detect a location of the traceable micro-electro-mechanical system in the wellbore based on a backscatter response of the at least one thermal neutron adsorbing material to the neutron log;

thereafter sensing one or more parameters in the wellbore with the traceable micro-mechanical system, wherein the one or more parameters comprises at least one measurement selected from the group consisting of temperature, pH, moisture content, ion concentration, stress, strain, and combinations thereof; and correlating the one or more parameters provided by the traceable micro-electro-mechanical system with a determined position of the traceable micro-electro-mechanical system based on the neutron log.

2. A method according to claim 1, wherein the at least one thermal neutron absorbing material is attached to the outer surface of the housing thereof and is selected from the group consisting of gadolinium, iridium, boron nitride, boric acid, zinc borate, borax, gadolinium oxide, gadolinium acetate, gadolinium concentrated glass, and any combination thereof.

3. A method according to claim 1, wherein the at least one thermal neutron absorbing material is selected from the group consisting of cadmium, boron, gadolinium, iridium, boron carbide, boron nitride, boric acid, boron concentrated glass, zinc borate, borax, gadolinium oxide, gadolinium acetate, gadolinium concentrated glass, and any combination thereof.

4. A method according to claim 1, wherein the traceable micro-electro-mechanical system is 3 mm$^2$ or smaller.

5. A method according to claim 1, wherein the traceable micro-electro-mechanical system is present in the treatment fluid in an amount of 0.01 weight percent to 5 weight percent.

6. A method according to claim 1, wherein the treatment fluid is a drilling fluid, fracturing fluid, completion fluid, spacer fluid, lost circulation fluid, displacement fluid, drill-in fluid, or any combination thereof.

7. A method according to claim 1, wherein the treatment fluid further comprises a hydraulic cement and water, and wherein the method further comprises allowing the treatment fluid to set in the wellbore.

8. A method according to claim 7, wherein the treatment fluid is used in primary cementing.

9. A method according to claim 1, wherein the introducing comprises pumping the treatment fluid through a casing and into a wellbore annulus.

10. A method according to claim 1, further comprising determining a top of cement based at least on the determined position of the traceable micro-electro-mechanical system.

11. The method of claim 1, wherein the housing is formed at least partially from the thermal neutron absorbing material.

12. A method comprising:
introducing a cement composition into a wellbore, wherein the cement composition comprises a cement, water, and a traceable micro-electro-mechanical system, wherein the traceable micro-electro-mechanical system comprises a micro-electro-mechanical system comprising a housing, wherein the housing comprises an outer surface with one or more sides, wherein the one or more sides consists of a first side and a plurality of remaining sides, wherein at least one thermal neutron absorbing material is incorporated into the housing thereof or attached to the outer surface of the housing thereof, wherein the first side comprises the at least one thermal neutron absorbing material, and wherein the plurality of remaining sides do not comprise the at least one thermal neutron absorbing material;

allowing the cement composition to set in a wellbore annulus;

running a neutron log in the wellbore to detect a location of the traceable micro-electro-mechanical system in the wellbore based on a response of the thermal neutron absorbing material to the neutron log;

thereafter sensing one or more parameters in the wellbore with the traceable micro-electro-mechanical system, wherein the one or more parameters comprise at least a parameter other than the location; and correlating the one or more parameters provided by the traceable micro-electro-mechanical system with a determined position of the traceable micro-electro-mechanical system based on the neutron log.

13. A method according to claim 12, wherein the at least one thermal neutron absorbing material is selected from the group consisting of cadmium, boron, gadolinium, iridium, boron carbide, boron nitride, boric acid, boron concentrated glass, zinc borate, borax, gadolinium oxide, gadolinium acetate, gadolinium concentrated glass, and any combination thereof.

14. A method according to claim 12, wherein the traceable micro-electro-mechanical system is 3 mm$^2$ or smaller, and wherein the traceable micro-electro-mechanical system is present in the cement composition in an amount of 0.01 weight percent to 5 weight percent, and wherein the introducing comprises pumping the cement composition through a casing and into the wellbore annulus.

15. A method according to claim 12, further comprising determining a top of cement based at least on the determined position of the traceable micro-electro-mechanical system.

16. A method according to claim 12, wherein the one or more parameters comprise at least one cement characteristic selected from the group consisting of stress, strain, and combinations thereof.

17. The method of claim 12, comprising transmitting the one or more parameters from the traceable micro-electro-mechanical system with an antenna on the traceable micro-electro-mechanical system.

18. The method of claim 12, wherein the housing is formed at least partially from the thermal neutron absorbing material.

19. A method comprising:
introducing a treatment fluid comprising a traceable micro-electro-mechanical system into a wellbore, wherein the traceable micro-electro-mechanical system comprises a micro-electro-mechanical system comprising a housing, wherein the housing comprises and outer surface with one or more sides, wherein the one or more sides consists of a first side and a plurality of remaining sides, wherein at least one thermal neutron absorbing material is incorporated into the housing thereof, wherein the first side comprises the at least one thermal neutron absorbing material, and wherein the plurality of remaining sides do not comprise the at least one thermal neutron absorbing material, and wherein the at least one thermal neutron absorbing material is selected from the group consisting of cadmium, boron, gadolinium, iridium, boron carbide, boron nitride, boric acid, boron concentrated glass, zinc borate, borax, gadolinium oxide, gadolinium acetate, gadolinium concentrated glass, and any combination thereof;

running a neutron log in the wellbore to detect a location of the traceable micro-electro-mechanical system in the wellbore based on a response of the at least one thermal neutron adsorbing material to the neutron log;

thereafter sensing one or more parameters in the wellbore with the traceable micro-mechanical system, wherein the one or more parameters comprise at least a parameter other than the location;

transmitting the one or more parameters from the traceable micro-electro-mechanical system with an antenna on the micro-electro-mechanical system; and correlating the one or more parameters provided by the traceable micro-electro-mechanical system with a determined position of the traceable micro-electro-mechanical system based on the neutron log.

20. The method of claim 19, wherein the traceable micro-electro-mechanical system is 3 mm$^2$ or smaller.

\* \* \* \* \*